(12) United States Patent
Krochmal et al.

(10) Patent No.: US 7,671,071 B2
(45) Date of Patent: Mar. 2, 2010

(54) POLYMORPHIC FORM XVI OF FEXOFENADINE HYDROCHLORIDE

(75) Inventors: Barnaba Krochmal, Jerusalem (IL); Dov Diller, Jerusalem (IL); Ben-Zion Dolitzky, Petach Tiqva (IL); Judith Aronhime, Rehovot (IL); Shlomit Wizel, Petah Tiqva (IL); Boaz Gome, Rishon-Lezion (IL); Igor Lifshitz, Petach Tikva (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 711 days.

(21) Appl. No.: 11/243,496

(22) Filed: Oct. 3, 2005

(65) Prior Publication Data

US 2006/0217557 A1    Sep. 28, 2006

Related U.S. Application Data

(63) Continuation of application No. 10/459,688, filed on Jun. 10, 2003, now abandoned.

(60) Provisional application No. 60/387,972, filed on Jun. 10, 2002.

(51) Int. Cl.
*A61K 31/445*     (2006.01)
*C07D 211/22*     (2006.01)

(52) U.S. Cl. ............... 514/317; 546/239; 546/240

(58) Field of Classification Search ........... 514/317; 546/239, 340
See application file for complete search history.

(56) References Cited

U.S. PATENT DOCUMENTS

| | | | |
|---|---|---|---|
| 4,254,129 A | 3/1981 | Carr et al. | |
| 4,636,499 A | 1/1987 | Brändström et al. | |
| 4,659,716 A | 4/1987 | Villani et al. | |
| 4,929,605 A | 5/1990 | Domet et al. | |
| 5,375,693 A | 12/1994 | Woosley et al. | |
| 5,578,610 A | 11/1996 | D'Ambra | |
| 5,581,011 A | 12/1996 | D'Ambra | |
| 5,589,487 A | 12/1996 | D'Ambra | |
| 5,618,940 A | 4/1997 | King et al. | |
| 5,631,375 A | 5/1997 | King et al. | |
| 5,644,061 A | 7/1997 | King et al. | |
| 5,650,516 A | 7/1997 | King et al. | |
| 5,652,370 A | 7/1997 | King et al. | |
| 5,654,433 A | 8/1997 | King et al. | |
| 5,663,353 A | 9/1997 | King et al. | |
| 5,663,412 A | 9/1997 | D'Ambra | |
| 5,675,009 A | 10/1997 | King et al. | |
| 5,738,872 A * | 4/1998 | Ortyl et al. | .......... 424/452 |
| 5,750,703 A | 5/1998 | D'Ambra | |
| 5,855,912 A | 1/1999 | Ortyl et al. | |
| 5,925,761 A | 7/1999 | Senanayake et al. | |
| 5,932,247 A | 8/1999 | Ortyl et al. | |
| 5,990,127 A | 11/1999 | Meiwes et al. | |
| 5,994,549 A | 11/1999 | D'Ambra | |
| 6,037,353 A | 3/2000 | Woodward et al. | |
| 6,039,974 A | 3/2000 | MacLaren et al. | |
| 6,113,942 A | 9/2000 | Ortyl et al. | |
| 6,147,216 A | 11/2000 | Krauss et al. | |
| 6,153,754 A | 11/2000 | D'Ambra et al. | |
| 6,187,791 B1 | 2/2001 | Woodward et al. | |
| 6,201,124 B1 | 3/2001 | D'Ambra et al. | |
| 6,242,606 B1 | 6/2001 | Krauss et al. | |
| 6,340,761 B1 | 1/2002 | Krauss et al. | |
| 6,348,597 B2 | 2/2002 | Krauss et al. | |
| 6,399,632 B1 | 6/2002 | Woodward et al. | |
| 6,451,815 B1 | 9/2002 | Hwang et al. | |
| 6,548,675 B2 | 4/2003 | Krauss et al. | |
| 6,613,906 B1 | 9/2003 | Davies et al. | |
| 6,683,094 B2 | 1/2004 | Ayers | |
| 6,700,012 B2 | 3/2004 | Ayers | |
| 6,730,791 B2 | 5/2004 | Ayers | |
| 6,797,826 B2 | 9/2004 | D'Ambra et al. | |
| 6,815,549 B2 | 11/2004 | Castaldi et al. | |
| 6,903,232 B2 | 6/2005 | Dandala et al. | |
| 7,135,571 B2 | 11/2006 | Henten et al. | |
| 7,138,524 B2 | 11/2006 | McCarty et al. | |
| 7,390,906 B2 | 6/2008 | D'Ambra et al. | |
| 7,470,789 B2 | 12/2008 | Rao et al. | |
| 7,560,561 B2 | 7/2009 | D'Ambra et al. | |
| 2001/0012896 A1 | 8/2001 | Henton et al. | |
| 2001/0014741 A1 | 8/2001 | Henton et al. | |
| 2001/0025106 A1 | 9/2001 | Henton et al. | |
| 2002/0177608 A1 | 11/2002 | Dolitzky et al. | |
| 2002/0193603 A1 * | 12/2002 | Henton et al. | .............. 546/238 |
| 2003/0021849 A1 | 1/2003 | Dolitzky et al. | |
| 2003/0158227 A1 | 8/2003 | Krochmal et al. | |
| 2004/0077683 A1 | 4/2004 | Reddy et al. | |
| 2004/0248935 A1 | 12/2004 | Milla et al. | |
| 2005/0165056 A1 | 7/2005 | Kirsch et al. | |
| 2005/0256163 A1 | 11/2005 | Kor et al. | |
| 2005/0277775 A1 | 12/2005 | Castaldi et al. | |
| 2005/0282860 A1 | 12/2005 | Castaldi et al. | |
| 2006/0148851 A1 | 7/2006 | Wizel et al. | |
| 2007/0106078 A1 | 5/2007 | Sharma et al. | |
| 2007/0129401 A1 | 6/2007 | Henton et al. | |

FOREIGN PATENT DOCUMENTS

EP    1 260 505 A1    11/2002

(Continued)

OTHER PUBLICATIONS

Muzaffar et al. "Polymorphism and drug availability" J. Phar. 1(1) 59-66 (1979).*
Jain et al. "Polymorphisom in pharmacey" Indian Drugs 23(g)315-329 (1986).*
Doelker et al. "Crystalline modification . . . " CA 138:209993 (2002).*
Doelker et al. "Physicochemical behavior or active . . . " CA 132:325872 (2000).*

(Continued)

*Primary Examiner*—Celia Chang
(74) *Attorney, Agent, or Firm*—Kenyon & Kenyon LLP

(57) ABSTRACT

Provided is a crystalline (polymorphic) form of fexofenadine hydrochloride, denominated fexofenadine hydrochloride Form XVI.

24 Claims, 3 Drawing Sheets

FOREIGN PATENT DOCUMENTS

| | | |
|---|---|---|
| EP | 1 260 505 B1 | 3/2005 |
| EP | 1 614 681 A1 | 1/2006 |
| IN | 1309/MUM/2004 | 9/2004 |
| WO | WO 93/21156 | 10/1993 |
| WO | WO 95/31437 | 11/1995 |
| WO | WO 97/22344 | 6/1997 |
| WO | WO 00/01671 | 1/2000 |
| WO | WO 00/71124 A1 | 11/2000 |
| WO | WO 01/94313 A2 | 12/2001 |
| WO | WO 02/066429 A1 | 8/2002 |
| WO | WO 02/080857 A2 | 10/2002 |
| WO | WO 02/102777 A2 | 12/2002 |
| WO | WO 03/011295 A1 | 2/2003 |
| WO | WO 03/084510 A | 10/2003 |
| WO | WO 2004/067511 | 12/2004 |
| WO | WO 2005/019175 | 3/2005 |
| WO | WO 2007/007347 | 1/2007 |
| WO | WO 2007/049303 | 3/2007 |
| WO | WO 2007/052310 | 10/2007 |
| WO | WO 2007/135693 | 11/2007 |

OTHER PUBLICATIONS

Otsuka et al. "effect of polymorphic . . . " Chem. Pharm. Bull, 47(6) 852-856 (1999).*
Lanz et al. "Pharmaceutical powder technology . . . " (2006) p. 110.*
Singhal et al. "Drug polymorphism . . . " Advanced drug delivery reviews 56. p. 335-347 (2004).*
Berstein "Polymorphism in . . . " p. 115-118 (2002).*
Braga et al. "making crystals . . . " Chem. Commun. p. 3635-3645 (2005).*
Agrawala et al. "fexofenadine . . . " CA 147:79615 (2007).*
Tessler et al. "The methanol disolvate . . . " Acta Cryst. C61, p. 0707-0710 (2005).*
US Pharmacopia #23, National Formulary #18 (1995), Section (941) X-ray Diffraction, pp. 1843-1844.
Polymorphism in Pharmaceutical Solids, H.G. Brittain, Ed., Marcel Dekker, Inc. New York, 1999.
Dean, Analytical Chemistry Handbook, p. 10-23-10.26 (1995).
Rouhi, "The Right Stuff", Chem.Eng.News, Feb. 2003, p. 32-35 (2003).
Brittain, "Polymorphism in Pharmaceutical Solids", Marcel Dekker Inc. p. 141-163 (1999).
Seddon, "Pseudopolymorph: A Polemic" Crystal Growth and Design v.4(6) 1087 (2004).
Davidovich et al., "Detection of Polymorphism . . . " Am. Phar. Rev. v.7(1) pp. 10, 12, 14, 16, 100 (2004).
US 6,407,119, 06/2002, Ayers et al. (withdrawn)

* cited by examiner

POLYMORPHIC FORM XVI OF FEXOFENADINE HYDROCHLORIDE

CROSS REFERENCE TO RELATED APPLICATION

This application is a continuation of prior application U.S. Ser. No. 10/459,688, filed Jun. 10, 2003, now abandoned which claims the benefit under 35 U.S.C. § 119(e) of provisional application Ser. No. 60/387,972, filed Jun. 10, 2002, which is incorporated herein by reference.

FIELD OF THE INVENTION

The present invention relates to the solid state chemistry of fexofenadine hydrochloride and its use as an active pharmaceutical agent.

BACKGROUND OF THE INVENTION

4-[4-[4-(hydroxydiphenylmethyl)-1-piperidinyl]-1-hydroxybutyl]-α,α-dimethylbenzeneacetic acid of formula (I) (fexofenadine) is an $H_1$ receptor antagonist and a useful antihistaminic drug. It has low permeability into central nervous system tissues and weak antimuscarinic activity, causing it to have few systemic side effects.

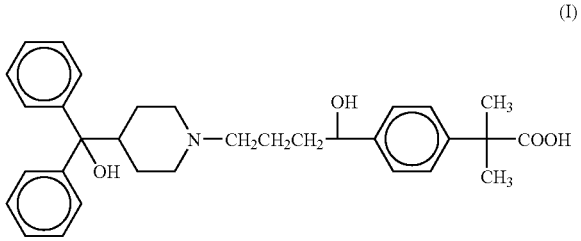

(I)

The antihistamic activity of fexofenadine is disclosed in U.S. Pat. No. 4,254,129, incorporated herein by reference. According to the '129 patent, fexofenadine can be prepared starting from ethyl α,α-dimethylphenyl acetate and 4-chlorobutyroyl chloride, which are reacted under Freidel-Crafts conditions. Chloride is displaced from the Freidel-Crafts product with α,α-diphenyl-4-piperidinemethanol to give 4-[4-[4-(hydroxydiphenylmethyl)-1-piperidinyl]-1-oxobutyl]-α,α-dimethylbenzeneacetate, which is isolated as its hydrochloride salt. The ketone is then reduced with $PtO/H_2$ and the ester group is hydrolyzed to yield fexofenadine hydrochloride.

Other methods of preparing fexofenadine are discussed in U.S. Pat. Nos. 5,578,610, 5,589,487, 5,581,011, 5,663,412, 5,750,703, 5,994,549, 5,618,940, 5,631,375, 5,644,061, 5,650,516, 5,652,370, 5,654,433, 5,663,353, 5,675,009, 5,375,693 and 6,147,216.

The present invention relates to the solid state physical properties, i.e., polymorphism, of fexofenadine hydrochloride. These properties may be influenced by controlling the conditions under which fexofenadine hydrochloride is obtained in solid form. Solid state physical properties include, for example, the flowability of the milled solid. Flowability affects the ease with which the material is handled during processing into a pharmaceutical product. When particles of the powdered compound do not flow past each other easily, a formulation specialist must take that fact into account when developing a tablet or capsule formulation, which may necessitate the use of glidants such as colloidal silicon dioxide, talc, starch or tribasic calcium phosphate.

Another important solid state property of a pharmaceutical compound is its rate of dissolution in aqueous fluid. The rate of dissolution of an active ingredient in a patient's stomach fluid may have therapeutic consequences because it imposes an upper limit on the rate at which an orally-administered active ingredient may reach the bloodstream. The rate of dissolution is also a consideration in formulating syrups, elixirs and other liquid medicaments. The solid state form of a compound may also affect its behavior on compaction and its storage stability.

These practical physical characteristics are influenced by the conformation and orientation of molecules in the unit cell, which defines a particular polymorphic form of a substance. The polymorphic form may give rise to thermal behavior different from that of the amorphous material or another polymorphic form. Thermal behavior is measured in the laboratory by such techniques as capillary melting point, thermogravimetric analysis (TGA) and differential scanning calorimetry (DSC), and may be used to distinguish some polymorphic forms from others. A particular polymorphic form may also give rise to distinct properties that may be detectable by powder X-ray diffraction, solid state 13C NMR spectrometry and infrared spectrometry.

U.S. Pat. Nos. 5,738,872, 5,932,247 and 5,855,912, incorporated herein by reference, describe four crystal forms of fexofenadine hydrochloride which are designated Forms I-IV. According to the '872 and related patents, Forms II and IV are hydrates and Forms I and III are anhydrates. Each form is characterized by its melting point, onset of endotherm in the DSC profile, and PXRD. Form I is reported to have a capillary melting point range of 196-201° C., a DSC endotherm with onset between 195-199° C. and a powder X-ray diffraction ("PXRD") pattern with d-spacings of 14.89, 11.85, 7.30, 6.28, 5.91, 5.55, 5.05, 4.96, 4.85, 4.57, 4.45, 3.94, 3.89, 3.84, 3.78, 3.72, 3.63, 3.07, 3.04, 2.45 Å. Form II is reported to have a capillary melting point range of 100-105° C., a DSC endotherm with onset between 124-126° C. and a PXRD pattern with d-spacings of 7.8, 6.4, 5.2, 4.9, 4.7, 4.4, 4.2, 4.1, 3.7, 3.6, 3.5 Å. Form III is reported to have a capillary melting point range of 166-171° C., a DSC endotherm with onset at 166° C. and a PXRD pattern with d-spacings of 8.95, 4.99, 4.88, 4.75, 4.57, 4.47, 4.46, 3.67, 3.65 Å. In Example 2, Form IV is reported to undergo decomposition at 115-116° C. In the general written description, a DSC endotherm with onset at 146° C. is reported. Form IV is reported as having a PXRD pattern with d-spacings of 10.38, 6.97, 6.41, 5.55, 5.32, 5.23, 5.11, 4.98, 4.64, 4.32, 4.28, 4.12, 4.02, 3.83, 3.65, 3.51, 3.46 and 2.83 Å.

The '872 patent discusses methods of interconverting Forms I-IV. Aqueous recrystallization of Form I can be used to produce Form II. Water-minimizing recrystallization or azeotropic distillation of either Form II or Form IV can yield Form I. Form III is reported to be accessible by water minimizing recrystallization of Form II. Crystal digestion of Form III can be used to obtain Form I. Forms II and IV can be obtained directly by sodium borohydride reduction of 4-[4-[4-(hydroxydiphenylmethyl)-1-piperidinyl]-1-oxobutyl]-α,α-dimethylbenzeneacetate as described in Examples 1 and 2.

International Publication No. WO 00/71124 A1, discloses that amorphous fexofenadine hydrochloride can be prepared by lyophilizing or spray drying a solution of fexofenadine hydrochloride. The product is characterized by its IR spectrum and a featureless PXRD pattern.

International Publication Nos. WO 01/94313 and WO 02/066429 are also directed to polymorphic forms of fexofenadine hydrochloride.

Fexofenadine hydrochloride Forms V, VI, and VIII through XV are disclosed in US 20030021849 and US 20020177608 (WO02/080857), both of which are incorporated herein by reference.

There is a need in the art for additional polymorphic forms of fexofenadine hydrochloride.

SUMMARY OF THE INVENTION

In one aspect, the present invention provides a crystalline fexofenadine hydrochloride in the solid state characterized by data selected from the group consisting of: a PXRD pattern with peaks at 10.1, 15.2, 18.6, 19.2, 20.1±0.2 degrees two theta; a DSC profile with two endothermic peaks at a temperature range of up to about 125° C. and an additional endotherm at a temperature of about 135° C.; and a TGA thermogram with a loss on drying (LOD) of about 6% to about 10% at a temperature range of up to about 145° C.

In another aspect, the present invention provides pharmaceutical formulations of fexofenadine hydrochloride Form XVI and their methods of administration.

In another aspect, the present invention provides a process for preparing crystalline fexofenadine hydrochloride Form XVI comprising the steps of combining fexofenadine free base, HCl and methanol to obtain a solution, precipitating fexofenadine hydrochloride in the presence of methanol and recovering the fexofenadine hydrochloride.

In another aspect, the present invention provides a process for preparing crystalline fexofenadine hydrochloride Form XVI comprising the steps of combining fexofenadine base, HCl and methanol to obtain a solution, evaporating the methanol to obtain a residue, adding methanol and a $C_5$ to $C_{12}$ hydrocarbon to the residue to precipitate fexofenadine hydrochloride and recovering the fexofenadine hydrochloride.

In another aspect, the present invention provides a process for preparing crystalline fexofenadine hydrochloride Form XVI comprising the steps of combining a solution of HCl in a mixture of methanol and isopropyl alcohol, with fexofenadine base, to obtain a solution, evaporating the methanol and the isopropyl alcohol to obtain a residue, adding a mixture of methanol and heptane to the residue to precipitate crystalline fexofenadine hydrochloride and recovering the fexofenadine hydrochloride.

In another aspect, the present invention provides a process for preparing crystalline fexofenadine hydrochloride Form XVI comprising the steps of combining fexofenadine free base, HCl and methanol to obtain a solution, removing the methanol to concentrate the solution, seeding the solution with fexofenadine hydrochloride Form XVI, stirring the solution, cooling the solution and recovering the fexofenadine hydrochloride.

In another aspect, the present invention provides a process for preparing fexofenadine hydrochloride Form XVI comprising the step of stirring a slurry of fexofenadine hydrochloride amorphous in methanol for a sufficient time to obtain fexofenadine hydrochloride Form XVI.

In another aspect, the present invention provides for a crystalline form of fexofenadine hydrochloride characterized by a PXRD pattern with peaks at 10.1, 15.2, 18.6, 19.2, 20.1±0.2, wherein the crystalline form has a water content of from about 6% to about 10%.

In another aspect, the present invention provides for a crystalline form of fexofenadine hydrochloride characterized by a PXRD pattern with peaks at 10.1, 15.2, 18.6, 19.2, 20.1±0.2, wherein the crystalline form with said PXRD peaks is substantially stable under storage at relative humidity of about 100% for at least about 1 week, and storage at about 40° C. and about a 75% relative humidity for at least about 6 months.

In another aspect, the present invention provides for a process for preparing a crystalline form of fexofenadine hydrochloride having a PXRD pattern with peaks at 10.1, 15.2, 18.6, 19.2, 20.1±0.2, comprising the steps of crystallizing the crystalline form with said PXRD peaks from a solution of fexofenadine hydrochloride in methanol and recovering the crystalline form.

DETAILED DESCRIPTION OF THE INVENTION

As used herein, "MTBE" refers to methyl t-butyl ether (syn. t-butyl methyl ether).

Figure 1:
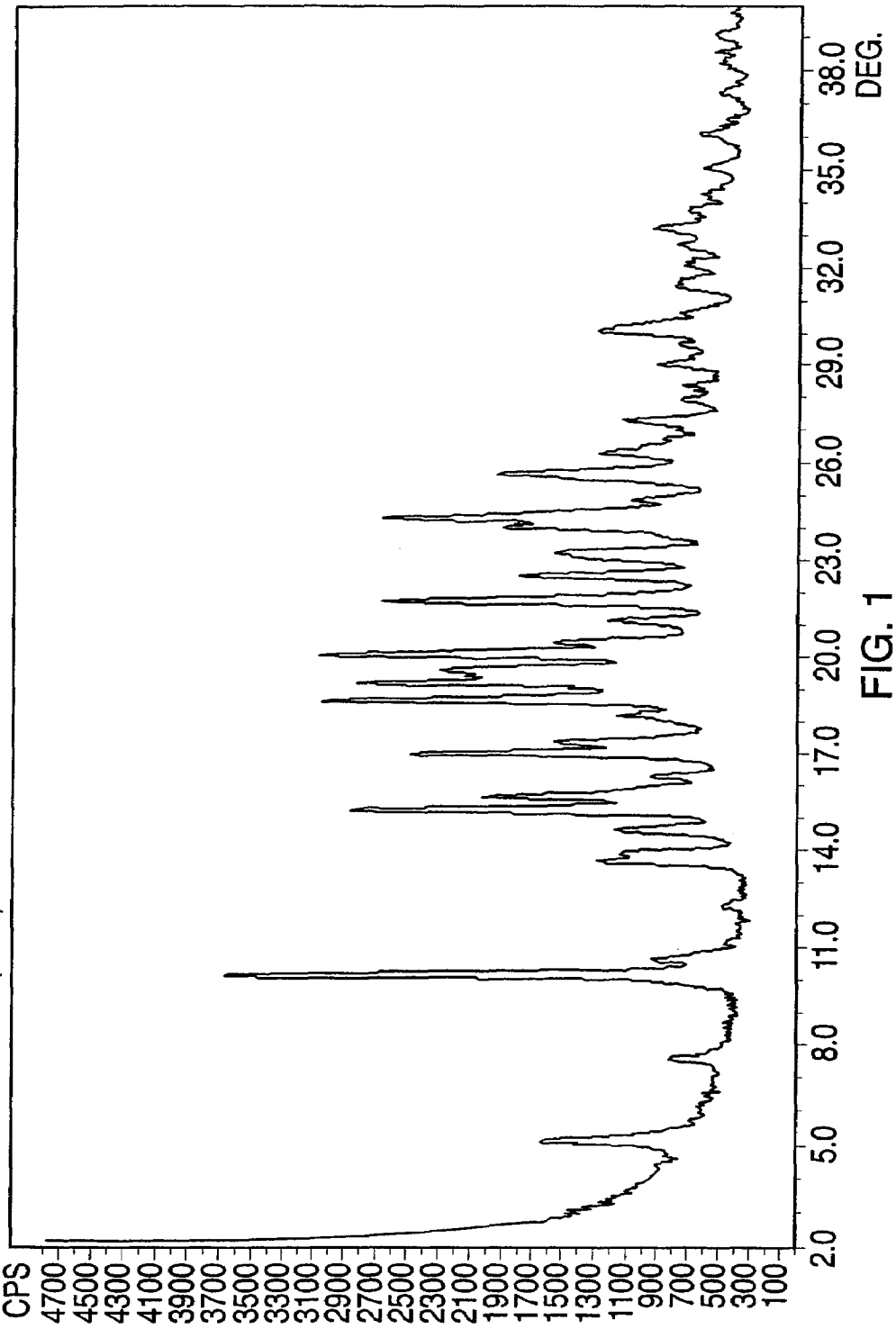
FIG. 1 is a PXRD pattern for fexofenadine hydrochloride Form XVI.

In one aspect, the present invention provides for fexofenadine hydrochloride Form XVI. Fexofenadine hydrochloride Form XVI is characterized by a PXRD pattern (FIG. 1) with peaks at 5.2, 10.1, 15.2, 15.5, 17.0, 17.3, 18.6, 19.2, 19.6, 20.1, 21.7, 22.5, 23.2, 24.0, 24.3, 25.6±0.2 degrees two theta. The most characteristic peaks are at 10.1, 15.2, 18.6, 19.2, 20.1±0.2 degrees two theta.

Fexofenadine hydrochloride Form XVI is also characterized by a DSC thermogram (FIG. 2) with two large endothermic peaks at a temperature range of up to about 125° C. and an additional small endotherm at a temperature of about 135° C. The first endothermic peak (≈75-85 J/g) is observed at a temperature of about 67° C., while the second endothermic peak (≈60 J/g) is observed at a temperature of about 120° C., and the third endothermic peak (≈0.3-2 J/g) is observed at a temperature of about 135° C.

Figure 3:
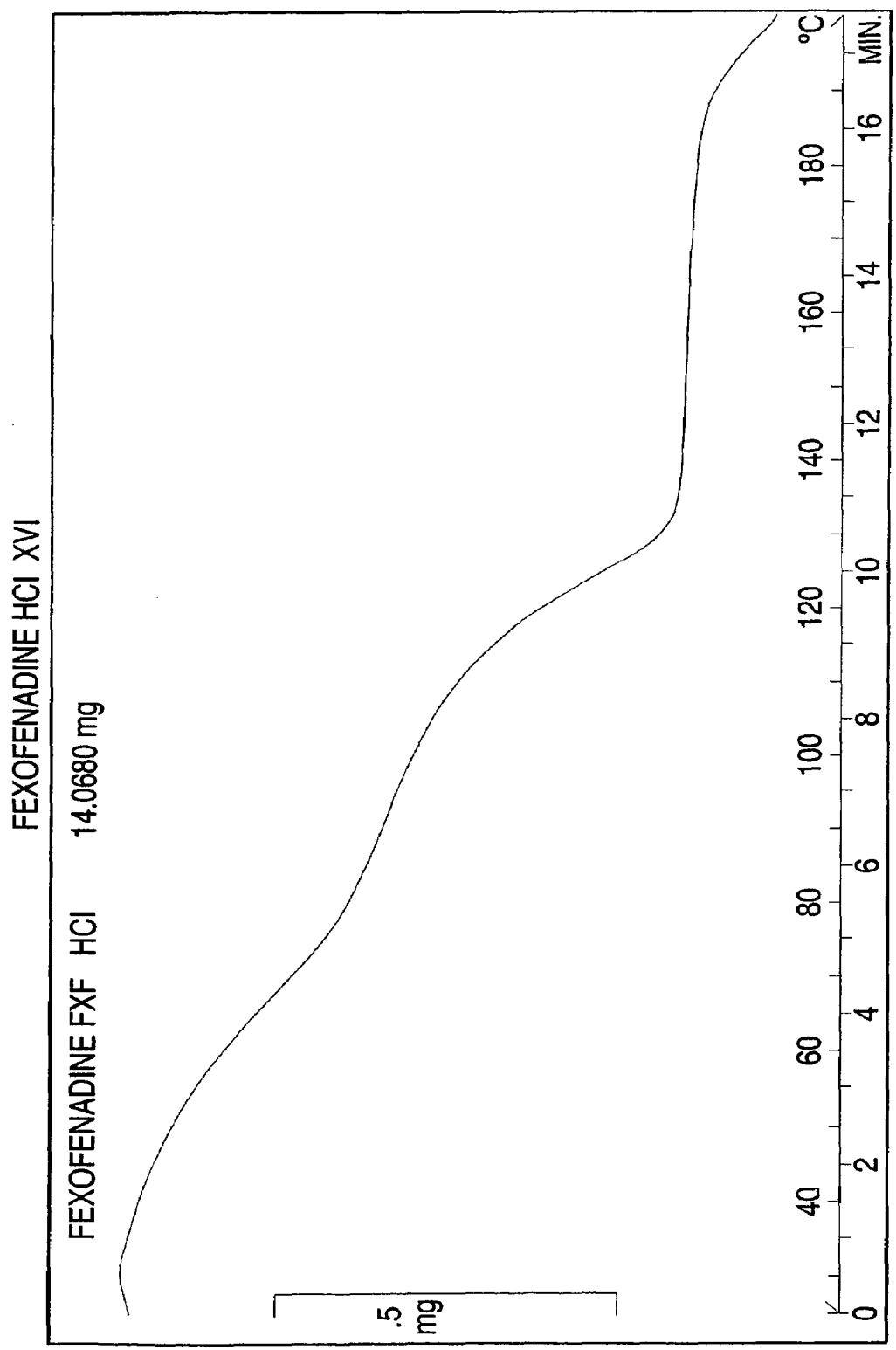
FIG. 3 is a TGA thermogram for fexofenadine hydrochloride Form XVI.

The TGA thermogram of fexofenadine HCl Form XVI (FIG. 3) shows an LOD value of about 6% to about 10% in a temperature range of up to 145° C.

Karl Fischer and elemental analysis of fexofenadine hydrochloride Form XVI point to a water content higher than an anhydrate. Fexofenadine hydrochloride Form XVI contains from about 6% to about 10% water by weight as measured by the Karl Fischer method. At the end of precipitation step, usually a Form XVI contains about 6% water by KF. But, the form absorbs water, and its water content may increase to as much as 10% water by weight.

Fexofenadine hydrochloride Form XVI is substantially stable during storage. Fexofenadine hydrochloride Form XVI is stable against transformation to other crystalline forms upon storage at relative humidity of up to about 100% for at least about 1 week, and storage at about 40° C. and about 75% relative humidity for at least about 6 months. The conversion is preferably less than about 5%, more preferably less than about 2% by weight.

In another aspect, the present invention provides for processes for preparation of fexofenadine hydrochloride Form XVI, which allow preparing fexofenadine HCl form XVI substantially free of other polymorphic forms of fexofenadine HCl, including amorphous form. As used herein, "substantially free" refers to less than about 5% on a weight basis, preferably less than about 2% weight, of polymorphic forms other than Form XVI compared to the weight of all the polymorphic forms, including Form XVI. A suitable method for determining the presence of other polymorphic forms is with X-Ray Powder diffraction.

In another aspect, the present invention provides for preparation of fexofenadine hydrochloride Form XVI by precipitation of the crystalline form from a methanol containing mixture. In the first step, a solution of fexofenadine hydrochloride in methanol is prepared. Subsequently, fexofenadine hydrochloride Form XVI may be recovered in various manners, such as by precipitation from the solution (including concentration of the solution before precipitation); or removal of the methanol to obtain a residue, followed by precipitation from methanol, or precipitation from a mixture of methanol and an anti-solvent. Precipitation may be carried out from both a slurry and a solution. When a residue is added to methanol, with or without an anti-solvent, generally a slurry is obtained.

In one embodiment, the present invention provides a process for preparing crystalline fexofenadine hydrochloride Form XVI comprising combining fexofenadine free base, HCl and methanol to obtain a solution, precipitating fexofenadine hydrochloride Form XVI from the solution, and recovering the fexofenadine hydrochloride Form XVI.

In another embodiment, the present invention provides a process for preparing the crystalline fexofenadine hydrochloride Form XVI comprising the steps of combining fexofenadine free base with HCl to obtain a solution in methanol, removing the methanol to obtain a residue, adding methanol and a $C_5$ to a $C_{12}$ hydrocarbon to the residue to cause precipitation of fexofenadine hydrochloride and recovering the fexofenadine hydrochloride. The addition of an anti-solvent such as a $C_5$ to a $C_{12}$ hydrocarbon is optional, i.e., the residue may only be taken up in methanol.

In one embodiment, a solution of HCl in a mixture of methanol and a polar organic solvent is added to fexofenadine base, preferably at a temperature of about 0 to about 10° C. An ice bath can be used to cool the solution. The resulting solution can be filtered to remove impurities, including any material that does not go into solution.

Suitable polar organic solvents are protic and aprotic polar solvents such as alcohols, ketones, esters and ethers. Preferred solvents include acetone and isopropanol. Preferably, a small amount of the polar solvent relative to methanol is used.

The solvent is then removed to obtain a residue. Preferably, the solvent is removed by evaporation, more preferably under reduced pressure. The temperature can be increased or the pressure reduced to accelerate the evaporation process. Preferably the pressure is reduced by an oil pump to remove the solvent by evaporation.

Fexofenadine hydrochloride Form XVI is then crystallized from methanol, or a mixture of methanol and a suitable anti-solvent, such as a $C_5$ to a $C_{12}$ saturated or a monoaromatic hydrocarbon. Examples of such hydrocarbons include heptane and hexane, with saturated hydrocarbons such as heptane being more preferred. Preferably the ratio of methanol to the hydrocarbon is from about 1:3 to about 1:33 (v/v). Preferably, the resulting mixture is stirred.

The fexofenadine hydrochloride so recovered is then preferably dried at a temperature of about 50° C. to about 80° C., more preferably at a temperature of from about 60° C. to about 70° C., most preferable under reduced pressure. Both the wet and the dried samples are fexofenadine hydrochloride Form XVI.

In another embodiment, fexofenadine hydrochloride Form XVI is prepared by concentrating the solution of fexofenadine hydrochloride in methanol before precipitation, preferably followed by seeding and cooling to precipitate Form XVI. In this embodiment, the solution is preferably concentrated to a level of about 2 to about 2.5 volumes of methanol in comparison to the weight of fexofenadine base (ml/g). The fexofenadine HCl methanol solution may optionally be filtered in order to remove foreign particles.

In a preferred embodiment, after the seeding step, the solution is stirred and cooled to enhance precipitation. After precipitation, the resulting suspension may optionally be stirred, preferably at a low temperature (about minus 15° C. to about 10° C.) for a sufficient amount of time, preferably for at least about 20 minutes, to increase the yield.

The fexofenadine hydrochloride so recovered is then preferably dried at a temperature of about 50° C. to about 80° C., more preferably at a temperature of from about 60° C. to about 70° C., most preferable under reduced pressure. Both the wet and the dried samples are fexofenadine hydrochloride Form XVI.

In another embodiment, the present invention provides for preparation fexofenadine hydrochloride Form XVI through stirring a slurry of amorphous fexofenadine hydrochloride in methanol. An anti-solvent may optionally be added to the methanol.

In one embodiment, the anti-solvent is a $C_5$ to $C_{12}$ hydrocarbon, more preferably a saturated hydrocarbon and most preferably heptane. Preferably a small amount of methanol compared to heptane is used, more preferably from about 3% to about 26% volume of methanol compared to volume of heptane. The slurry process is carried out for a sufficient time to obtain fexofenadine hydrochloride Form XVI. Preferably the slurry process is carried out for at least about 5 hours, more preferably for at least about 10 hours and most preferably for at least about 15 hours.

One skilled in the art would appreciate that the polymorphs of the present invention can be selectively obtained from fexofenadine hydrochloride generally through crystallization with different recrystallization solvent systems. The starting material can be anhydrous fexofenadine hydrochloride or any fexofenadine hydrochloride hydrate or lower alcohol solvate. The use of other solvates, such as the ethyl acetate solvate of the present invention, is not believed to interfere with the effectiveness of the process. The starting fexofenadine hydrochloride can also be in an amorphous or any crystalline crystal form. The process can be used as a purification method by using the desired form in an unacceptably pure state as starting material. The processes of the present invention can also be practiced as the last step in the methods discussed in U.S. Pat. Nos. 5,578,610, 5,589,487, 5,581,011, 5,663,412, 5,750,703, 5,994,549, 5,618,940, 5,631,375, 5,644,061, 5,650,516, 5,652,370, 5,654,433, 5,663,353, 5,675,009, 5,375,693 and 6,147,216 to prepare a novel polymorph of the present invention.

Many processes of the present invention involve crystallization out of a particular solvent. One skilled in the art would appreciate that the conditions concerning crystallization can be modified without affecting the form of the polymorph obtained. For example, when mixing fexofenadine hydrochloride or free base in a solvent to form a solution, warming of the mixture can be necessary to completely dissolve the starting material. If warming does not clarify the mixture, the mixture can be diluted or filtered. To filter, the hot mixture can be passed through paper, glass fiber or other membrane material, or a clarifying agent such as celite. Depending upon the equipment used and the concentration and temperature of the solution, the filtration apparatus may need to be preheated to avoid premature crystallization.

The conditions can also be changed to induce precipitation. A preferred way of inducing precipitation is to reduce the solubility of the solvent. The solubility of the solvent can be reduced, for example, by cooling the solvent.

In one embodiment, an anti-solvent is added to a solution to decrease its solubility for a particular compound, thus resulting in precipitation. In another embodiment, an anti-solvent is added to an oily residue or a gummy material, wherein the low solubility of the anti-solvent for a particular compound results in precipitation of that compound.

Another manner to accelerate crystallization is by seeding with a crystal of the product or scratching the inner surface of the crystallization vessel with a glass rod. Other times, crystallization can occur spontaneously without any inducement. The present invention encompasses both embodiments where precipitation happens spontaneously or is induced, unless if such inducement is critical for obtaining a particular polymorphic form of fexofenadine hydrochloride.

As an antihistamine, fexofenadine is effective at relieving symptoms caused by airborne and contact inducers of histamine release. Such substances include pollen, spores, animal dander, cockroach dander, industrial chemicals, dust and dust mites. Symptoms that can be alleviated by fexofenadine include bronchial spasms, sneezing, rhinorrhia, nasal congestion, lacrimation, redness, rash, urticaria and itch.

Fexofenadine hydrochloride Forms XVI useful for delivering fexofenadine to the gastrointestinal tract, mucus membranes, bloodstream and inflamed tissues of a patient suffering from inflammation caused by a histamine. They can be formulated into a variety of compositions for administration to humans and animals.

Pharmaceutical compositions of the present invention contain fexofenadine hydrochloride Form XVI, optionally in a mixture with other forms of amorphous fexofenadine and/or active ingredients such as pseudoephedrine. They can also be optionally mixed with pseudoephedrine. In addition to the active ingredient(s), the pharmaceutical compositions of the present invention can contain one or more excipients. Excipients are added to the composition for a variety of purposes.

Diluents increase the bulk of a solid pharmaceutical composition and can make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form like a tablet can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of non-compacted solid composition and improve the accuracy of dosing. Excipients that can function as glidants include colloidal silicon dioxide, magnesium trisilicate, powdered cellulose, starch, talc and tribasic calcium phosphate.

When a dosage form such as a tablet is made by compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, fexofenadine hydrochloride Form XVI and any other solid excipients are dissolved or suspended in a liquid carrier such as water, vegetable oil, alcohol, polyethylene glycol, propylene glycol or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar can be added to improve the taste.

Preservatives and chelating agents such as alcohol, sodium benzoate, butylated hydroxy toluene, butylated hydroxyanisole and ethylenediamine tetraacetic acid can be added at levels safe for ingestion to improve storage stability.

A liquid composition according to the present invention can also contain a buffer such as guconic acid, lactic acid, citric acid or acetic acid, sodium guconate, sodium lactate, sodium citrate or sodium acetate.

Selection of excipients and the amounts to use can be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages can be conveniently presented in unit dosage form and prepared by any of the methods well-known in the pharmaceutical arts.

Dosage forms include solid dosage forms like tablets, powders, capsules, suppositories, sachets, troches and losenges as well as liquid syrups, suspensions and elixirs.

A dosage form of the present invention is a capsule containing the composition, preferably a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filing can be prepared by wet granulation. In wet granulation some or all of the active ingredients and excipients in powder form are blended and then further mixed in the presence of a liquid, typically water, which causes the powders to clump up into granules. The granulate is screened and/or milled, dried and then screened and/or milled to the desired particle size. The granulate can then be tableted or other excipients can be added prior to tableting, such as a glidant and/or a lubricant.

A tableting composition can be prepared conventionally by dry blending. For instance, the blended composition of the actives and excipients can be compacted into a slug or a sheet and then comminuted into compacted granules. The compacted granules can be compressed subsequently into a tablet.

As an alternative to dry granulation, a blended composition can be compressed directly into a compacted dosage form using direct compression techniques. Direct compression produces a more uniform tablet without granules. Excipients that are particularly well-suited to direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, only they are not subjected to a final tableting step.

Capsules, tablets and lozenges and other unit dosage forms preferably contain a dosage level of about 30 to about 180 mg of fexofenadine hydrochloride. Other dosages may also be administered depending on the need.

The following describes the instrumentation used by the present invention to characterize the new polymorphs. The PXRD patterns (such as that for fexofenadine HCl Form XVI) were obtained by methods known in the art using a Scintag X-ray powder diffractometer, a variable goniometer, an X-Ray tube with Cu target anode (Cu radiation $\lambda=1.5418$ Å) and a solid state detector. A round standard aluminum sample holder with a round zero background quartz plate was used. Scans were performed over a range of 2 to 40 degrees two-theta, continuously, with a scan rate of 3 degrees/min.

The DSC thermogram was obtained using a DSC Mettler 821 Star. The temperature range of scans was 30-350° C. at a rate of 10° C./min. The weight of the sample was 2-5 mg. The sample was purged with nitrogen gas at a flow rate of 40 mL/min. Standard 40 $\Phi$l aluminum crucibles having lids with three small holes were used.

The TGA thermogram for fexofenadine hydrochloride Form XVI was performed on Mettler TG50 using standard allumina pan and a sample weight: 7-15 mg.

EXAMPLES

Example 1

Preparation of Fexofenadine Hydrochloride Form XVI

HCl/IPA (1.6 ml) (6.05-6.24 N) was added to methanol (20 ml) and was cooled in an ice water bath. This solution was added to fexofenadine free base (5 grams) in a round bottom flask with a magnetic stirrer in an ice bath. The fexofenadine base dissolved immediately. The solution was filtered thru a glass fiber filter (GF/F), and the solvent evaporated off in a water bath at a temperature of 25° C. using a water aspirator, followed by a diaphragm pump, which was followed by an oil pump. Heptane (15 ml) was added. The stirrer was turned on, 5 ml of methanol was added and the slurry was stirred overnight. The next day it was filtered and dried in the vacuum oven for 2 hours at 65° C. PXRD analysis confirmed presence of Form XVI of fexofenadine hydrochloride.

KF=6.685%

Elemental analysis: C, 66.28%; H, 7-89%; Cl, 5.65%.

Example 2

Preparation of Fexofenadine Hydrochloride Form XVI

Example 1 was repeated, except 4 ml of methanol was used in the crystallization step instead of 5 ml. PXRD analysis confirmed presence of Form XVI of fexofenadine hydrochloride.

KF=6.507%

Elemental analysis: C, 66.80%; H, 7.91%; Cl, 6.23%.

Example 3

Preparation of Fexofenadine Hydrochloride Form XVI

Example 1 was repeated, except 3 ml of methanol was used in the crystallization step instead of 5 ml. PXRD analysis confirmed presence of Form XVI of fexofenadine hydrochloride.

KF=6.221%

Elemental analysis: C, 67.18%; H, 7.74%; Cl, 6.35%.

Example 4

Preparation of Fexofenadine Hydrochloride Form XVI

Example 1 was repeated, except 2 ml of methanol was used in the crystallization step instead of 5 ml. PXRD analysis confirmed presence of Form XVI of fexofenadine hydrochloride.

KF=7.314%

Elemental analysis: C, 65.95%; H, 7.77%; Cl, 6.34%.

Example 5

Preparation of Fexofenadine Hydrochloride Form XVI

Example 1 was repeated, except 2.5 ml of methanol was used in the crystallization step instead of 5 ml. PXRD analysis confirmed presence of Form XVI of fexofenadine hydrochloride.

KF=6.250%

Elemental analysis: C, 66.70%; H, 7.64%; Cl, 6.40%.

Example 6

Preparation of Fexofenadine Hydrochloride Form XVI

Fexofenadine free base (20 grams) was crushed and put into a 250 ml round bottom flask in an ice bath with a magnetic stirrer. HCl/IPA (6.5 ml) was added to 80 ml methanol and cooled in an ice bath, and then added to the flask with mixing. After 15 minutes, the flask was filtered, and the filtrate evaporated off at room temperature first with a water aspirator then with a diaphragm pump and finally with an oil pump. The remaining material (5 grams) was stirred as a slurry overnight with a mixture of heptane (15 ml) and methanol (1.5 ml), filtered and dried for 1 hour at 65° C. under vacuum. PXRD analysis confirmed presence of Form XVI of fexofenadine hydrochloride.

Example 7

Process for Preparation of Fexofenadine-HCl Form XVI by Crystallization from Methanol

Step 1: Preparation of HCl Gas Solution in Methanol

HCl gas was dissolved in cold methanol (T<10° C.), until about 5% w/w concentration was achieved.

Step 2: Dilution of HCl/Methanol Solution

Methanol/HCl solution (79.9 grams) (4.5 w/w) was diluted with 121.8 grams of methanol to obtain diluted HCl/methanol solution.

Step 3: Titration of Fexofenadine-Base with Diluted HCl/Methanol solution

The diluted HCl/methanol solution was cooled (T<10° C.). Fexofendine base (50 grams) (1.88% $H_2O$) was reacted with the diluted HCl/methanol solution, to form a fexofenadine-HCl solution. The molar ratio between fexofenadine-base and HCl was 1:1.

Step 4: Removal of Particulate Matter

The fexofenadine-HCl solution was filtered under reduced pressure to remove particulate matter (foreign particles).

Alternative A—Step 5: Isolation of the Product

The clear solution was distilled under reduced pressure at a jacket temperature of not more than 40° C. until the ratio of the residual solvent in the reactor was 2 to 2.5 volumes vs. the weight of fexofenadine base (ml/g).

After the final solvent volume was reached, the solution was seeded with fexofenadine HCl Form XVI crystals, and then stirred for an additional 30 to 90 minutes. The seeded solution was cooled and kept at a temperature of 0 to 10° C. for at least 4 hours, and the slurry was stirred for an additional 30 to 90 minutes. The solid was separated from the mother liquor by filtration under reduced pressure. The wet product was dried under reduce pressure at a temperature of 50-65° C.

Alternative B—Step 5: Isolation of the Product

The clear solution was distilled under reduced pressure at a jacket temperature not more than 40° C. until there was no more distillate. Methanol in the ratio of 2 to 2.5 volumes vs. the weight of fexofenadine base was added to the reactor (ml/g), and the fexofenadine HCl in methanol mixture was heated to dissolution.

After the final solvent volume was reached, the solution was seeded with fexofenadine HCl Form XVI crystals, and then stirred for an additional 30 to 90 minutes. The seeded solution was cooled and kept at a temperature of 0 to 10° C. for at least 4 hours, and the slurry was stirred for an additional 30 to 90 minutes. The solid was separated from the mother liquor by filtration under reduced pressure. The wet product was dried under reduce pressure at a temperature of 50-65° C.

Example 8

Preparation of Fexofenadine Hydrochloride Form XVI From Amorphous Form

Amorphous fexofenadine HCl (5 gr) was stirred in a mixture of heptane (15 ml) and methanol (1.5 ml) at room temperature. After stirring overnight, a solid was filtered and dried at 65° C. The PXRD pattern of the solid confirmed that the product was fexofenadine hydrochloride Form XVI.

Having thus described the invention with reference to particular preferred embodiments and illustrated it with examples, those in the art will appreciate modifications to the invention as described and illustrated that do not depart from the spirit and scope of the invention as disclosed in the specification. All the references cited herein are incorporated by reference in their entirety.

What is claimed is:

1. Crystalline fexofenadine hydrochloride Form XVI characterized by a PXRD pattern having peaks at 10.1, 15.2, 18.6, 19.2 and 20.1±0.2 degrees two theta, wherein the crystalline fexonfenadine hydrochloride has a water content of about 6% to about 10%.

2. The crystalline fexofenadine hydrochloride of Form XVI claim 1, further characterized by a DSC thermogram having three endothermic peaks at about 67° C., about 120° C. and about 135° C.

3. The crystalline fexofenadine hydrochloride Form XVI of claim 2, wherein the DSC thermogram is as substantially depicted in FIG. 2.

4. The crystalline fexofenadine hydrochloride Form XVI of claim 1, further characterized by the PXRD pattern having peaks at 5.2, 15.5, 17.0, 17.3, 19.6, 21.7, 22.5, 23.2, 24.0, 24.3 and 25.6±0.2 degrees two theta.

5. The crystalline fexofenadine hydrochloride Form VI of claim 4, further characterized by a PXRD pattern as substantially depicted in FIG. 1.

6. The crystalline fexofenadine hydrochloride Form XVI of claim 5, further characterized by a DSC thermogram as substantially depicted in FIG. 2.

7. The crystalline fexofenadine hydrochloride Form VI of claim 2, further characterized by a DSC thermogram having three endothermic peaks at about 67° C., about 120° C. and about 135° C.

Figure 2:
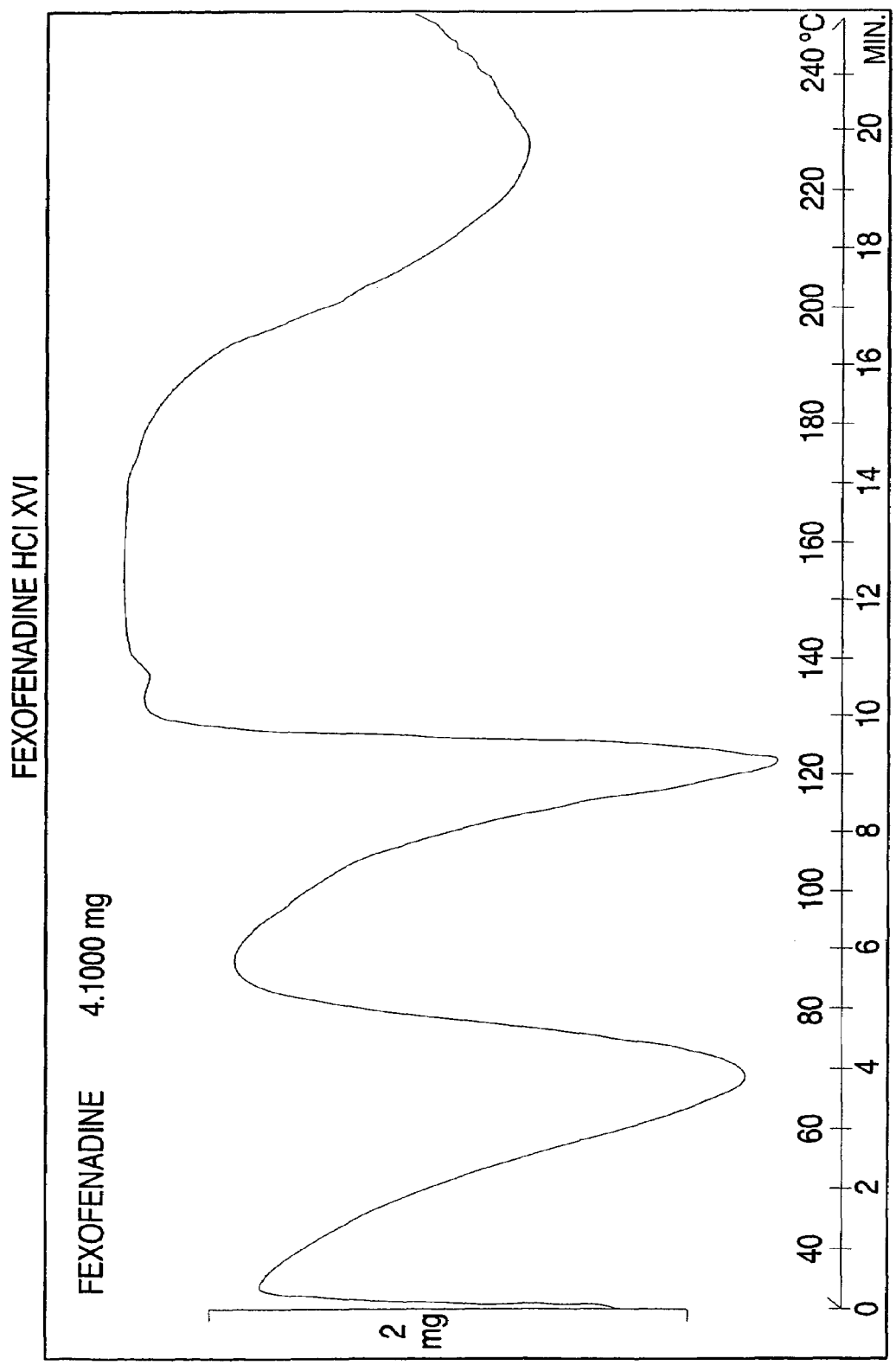
FIG. 2 is DSC thermogram for fexofenadine hydrochloride Form XVI.

8. The crystalline fexofenadine hydrochloride Form VI of claim 7, wherein the DSC thermogram is substantially as depicted in FIG. 2.

9. Crystalline fexofenadine hydrochloride Form VI characterized by a DSC thermogram having three endothermic peaks at about 67° C., about 120° C. and about 135° C., wherein the crystalline fexonfenadine hydrochloride has a water content of about 6% to about 10%.

10. The crystalline fexofenadine hydrochloride Form XVI of claim 9, wherein the DSC thermogram is substantially as depicted in FIG. 2.

11. A pharmaceutical formulation comprising an effective amount Form XVI of crystalline fexofenadine hydrochloride Form XVI having a PXRD pattern with peaks at 10.1, 15.2, 18.6, 19.2 and 20.1±0.2 degrees two theta, and a pharmaceutically acceptable excipient, wherein the crystalline fexonfenadine hydrochloride has a water content of about 6% to about 10%.

12. The pharmaceutical formulation of claim 11, wherein the crystalline form XVI is characterized by a DSC profile with two endothermic peaks at a temperature range of up to about 125° C. and an additional endotherm at a temperature of about 135° C.

13. The pharmaceutical formulation of claim 12, wherein one of the two endothermic peaks is at a temperature of about 67° C. and the other at a temperature of about 120° C.

14. The pharmaceutical formulation of claim 11, wherein the crystalline form XVI is characterized by a DSC thermogram as substantially depicted in FIG. 2.

15. The pharmaceutical formulation of claim 11, wherein the crystalline form XVI is further characterized by a PXRD pattern with peaks at 5.2, 15.5, 17.0, 17.3, 19.6, 21.7, 22.5, 23.2, 24.0, 24.3 and 25.6±0.2 degrees two theta.

16. The pharmaceutical formulation of claim 11, wherein the crystalline form XVI is characterized by a PXRD pattern as substantially depicted in FIG. 1.

17. The pharmaceutical formulation of claim 11 substantially free of other polymorphic forms of fexofenadine hydrochloride, wherein the crystalline fexofenadine hydrochloride contains less than about 5 weight % of other polymorphic forms of fexofenadine hydrochloride based on the total weight of all the polymorphic forms of fexofenadine hydrochloride present.

18. The pharmaceutical formulation of claim 11 having less than about 2% by weight of other polymorphic forms of fexofenadine hydrochloride.

19. The pharmaceutical formulation of claim 11, wherein the crystalline form has about 10% water by weight.

20. The pharmaceutical formulation of claim 11, wherein the crystalline form with said PXRD peaks is substantially stable under storage at relative humidity of about 100% for at least about 1 week, and storage at about 40° C. and about a 75% relative humidity for at least about 6 months.

21. A method of inhibiting binding between an $H_1$ receptor and histamine in a patient suffering from contraction of the bronchi, vasodilation, itching or other inflammation response to histamine comprising administering to the patient the pharmaceutical composition of claim 11.

22. A method for preparing a pharmaceutical formulation comprising combining crystalline fexofenadine hydrochloride Form XVI having a PXRD pattern with peaks at 10.1, 15.2, 18.6, 19.2 and 20.1±0.2 degrees two theta with a pharmaceutically acceptable excipient.

23. A pharmaceutical formulation prepared by the method of claim 22.

24. The pharmaceutical formulation of claim 11, further comprising pseudoephedrine hydrochloride.

* * * * *

UNITED STATES PATENT AND TRADEMARK OFFICE
CERTIFICATE OF CORRECTION

PATENT NO. : 7,671,071 B2
APPLICATION NO. : 11/243496
DATED : March 2, 2010
INVENTOR(S) : Krochmal et al.

Page 1 of 1

It is certified that error appears in the above-identified patent and that said Letters Patent is hereby corrected as shown below:

Column 12: in claim 5, line 1, change "Form VI" to --Form XVI--

Column 13: in claim 7, line 1, change "Form VI" to --Form XVI--

Column 13: in claim 8, line 1, change "Form VI" to --Form XVI--

Column 13: in claim 9, line 1, change "Form VI" to --Form XVI--

Signed and Sealed this

Twenty-seventh Day of July, 2010

David J. Kappos
*Director of the United States Patent and Trademark Office*

UNITED STATES PATENT AND TRADEMARK OFFICE
CERTIFICATE OF CORRECTION

PATENT NO. : 7,671,071 B2
APPLICATION NO. : 11/243496
DATED : March 2, 2010
INVENTOR(S) : Krochmal et al.

It is certified that error appears in the above-identified patent and that said Letters Patent is hereby corrected as shown below:

Column 12 line 65 (claim 5, line 1), change "Form VI" to --Form XVI--

Column 13 line 4 (claim 7, line 1), change "Form VI" to --Form XVI--

Column 13 line 8 (claim 8, line 1), change "Form VI" to --Form XVI--

Column 13 line 11 (claim 9, line 1), change "Form VI" to --Form XVI--

This certificate supersedes the Certificate of Correction issued July 27, 2010.

Signed and Sealed this

Twenty-fourth Day of August, 2010

David J. Kappos
*Director of the United States Patent and Trademark Office*